United States Patent [19]

Magorien

[11] 4,150,575
[45] Apr. 24, 1979

[54] FLUID SAMPLER AND MINIMUM-INCLUDED-AIR-COUPLING

[75] Inventor: Vincent G. Magorien, Granada Hills, Calif.

[73] Assignee: Systron-Donner Corporation, Concord, Calif.

[21] Appl. No.: 860,302

[22] Filed: Dec. 14, 1977

[51] Int. Cl.² .................... F16L 37/22; G01N 1/10
[52] U.S. Cl. ................... 73/422 R; 285/277
[58] Field of Search ............ 73/422 R, 421 B, 425.6; 285/277, 316

[56] References Cited

U.S. PATENT DOCUMENTS

| | | | |
|---|---|---|---|
| 3,174,508 | 3/1965 | Zahuranec | 285/277 X |
| 3,267,963 | 8/1966 | Hupp | 285/316 X |
| 3,778,092 | 12/1973 | Magorien | 285/316 |
| 3,791,411 | 2/1974 | Bogeskov et al. | 285/277 X |

Primary Examiner—Richard C. Queisser
Assistant Examiner—Joseph W. Roskos
Attorney, Agent, or Firm—Fulwider, Patton, Rieber, Lee & Utecht

[57] ABSTRACT

A coupling that permits a connection to be made to a fluid system with a minimum of included air, even though the coupled device is not pre-filled. The coupling is particularly advantageously employed as part of a sampler used to take fluid samples for analysis as to air content. It includes a valve housing, a valve seat slidable within the housing and a valve closure member slidable within the seat. A lost motion mechanism allows joint movement of the seat and closure member prior to disengagement of the seat from the closure member. The fluid passage by which fluid is withdrawn from the system extends through the closure member.

18 Claims, 4 Drawing Figures

1

FLUID SAMPLER AND MINIMUM-INCLUDED-AIR-COUPLING

BACKGROUND OF THE INVENTION

The present invention relates to couplings for fluid systems, and, more particularly, to a coupling for connecting to such a system a device, such as a sampler, that is not pre-filled. The invention further relates to an improved sampler which minimizes the amount of included air.

When any device is to be filled with fluid from a closed system, it is difficult to avoid contaminating the device or the system generally with included air. The term "included air" is used here to refer to air which is present within the coupling or its surroundings prior to connection and does not refer to air entrained or dissolved within the fluid. Thus, the term included air embraces all extraneous air that does not come from the system to be sampled; it embraces air from within the internal volume of the coupling and ambient air that becomes included as the coupling is connected.

The need to avoid included air is particularly important when a sampler is to be connected to the system to withdraw a sample of fluid which will later be analyzed to measure its entrained or dissolved air content. Samples are taken for this purpose from the working fluid of aircraft hydraulic systems and the oil in transformers, to name two examples.

There are several known couplings which are used to make connections to fluid systems, exemplary couplings being described in this inventor's previously issued U.S. Pat. Nos. 3,073,342 and 3,778,092. They employ an arrangement of a valve head surrounded by a conical valve seat. Upon engagement with a coupling receiver, the seat moves away from the head, permitting the fluid to flow through an annular opening between the seat and the head, parallel to a valve stem to which it is connected, and out the other end of the coupling. Flow in the opposite direction is also permitted.

These previously known couplings are primarily suitable for use in those situations in which fluid is present on both sides of the coupling, i.e., the device to be connected to the system is pre-filled, but could also be used in non-prefilled situations in which included air is of limited concern. It has been found, however, that the above-mentioned couplings do not perform satisfactorily when connected to a fluid sampler to be used to test a fluid for air content. A large volume of air that surrounds the valve stem, behind the valve seat and head, is drawn into the sampler along with the system fluid, and this included air makes accurate analysis of the system fluid impossible.

Other structurally different fluid couplings are known in which the coupling valve is formed by an inner member and a sleeve that slides axially on the inner member. The inner member has an axial passage that communicates with ports on its cylindrical sides. To open the valve, the sleeve is moved into a position in which the ports are exposed.

Previously known valves of this last-mentioned type have a relatively large internal volume within the ports and axial passage and, therefore, present the same included air problems as do those valves discussed above. A further disadvantage of these valves is that they rely upon O-rings to achieve a seal between the inner member and the sleeve, the forwardmost O-ring being engaged and disengaged as the valve is closed and opened. The member that engages and disengages this O-ring must have a chamfered leading edge if the O-ring seal is not to be worn excessively or otherwise damaged. The presence of this chamfered edge creates a void when the coupling is mated with the coupling receiver and this void is an additional source of included air.

There is at present a need for a fluid coupling that minimizes the amount of included air when a connection is made, particularly when the device to be connected is empty prior to connection. There is also a need for a sampler that is capable of withdrawing a fluid sample while minimizing contamination of the sample by included air. The objective of the present invention is to fill the above needs with an improved coupling that retains the important advantages of previously known fluid couplings, such as fast connection and disconnection, high reliability and freedom from fluid leakage.

SUMMARY OF THE INVENTION

The present invention resides in a fluid coupling that accomplishes the above objective. It includes a valve closure member that normally engages a surrounding valve seat but, when the coupling is connected to a coupling receiver of a fluid system, the seat is separated from the head permitting fluid to flow between the seat and the closure member. The fluid can then enter a cross-bore in the closure member leading to a small diameter axial bore by which it exits from the opposite end of the coupling. The adjoining outside faces of the closure member and the seat can be flush with each other, thereby avoiding the formation of a void where they meet.

It is advantageous to employ a valve housing in which the valve seat is axially slidable, lost motion taking place as the seat and closure member move together within the housing against the force of a spring. When movement of the closure member is arrested by a stop, the seat disengages from the closure member to open the valve.

Preferably, the valve seat has a conical shape opening toward the coupling receiver. The closure member has a tapered head shaped and dimensioned to mate with the seat and an elongated stem extending back from the head through the housing.

Another aspect of the invention relates to the use of the coupling described above as part of a fluid sampler. The sampler includes a housing in which a fluid receiver is slidably disposed. Fluid can be drawn into the receiver by a piston. The receiver is connected to the valve closure member and moves with it as permitted by the lost motion mechanism.

Other features and advantages of the present invention will become apparent from the following detailed description, taken in conjunction with the accompanying drawings, which illustrate, by way of example, the principles of the invention.

DESCRIPTION OF THE PREFERRED EMBODIMENT

Figure 1:
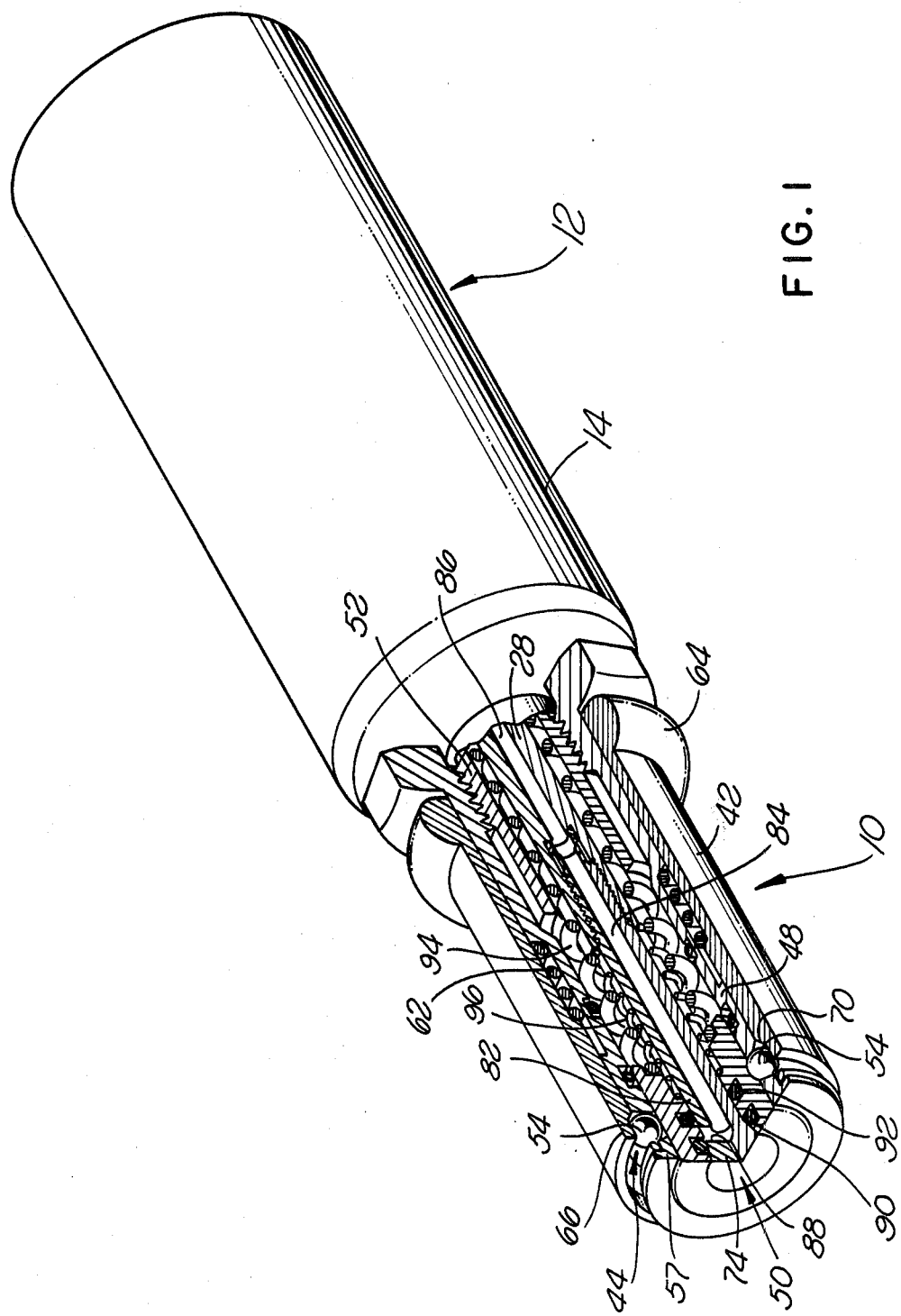
FIG. 1 is a partially broken away perspective view of a fluid sampler constructed in accordance with the current invention.

The present invention (shown in FIGS. 1–4) is embodied in a fluid coupling 10 and a sampler 12 in which the coupling is included. The purpose of the sampler 12 is to extract from a closed fluid system a fluid sample uncontaminated by a quantitiy of included air sufficient to distort the analysis of the sample beyond acceptable limits.

Apart from the coupling 10, the sampler 12 includes an elongated cylindrical housing 14 which is closed at its front end 16 except for a relatively small, centered, circular opening 18. The back end 20 of the housing 14 has a somewhat larger opening 22.

A fluid receiver 24 is slidably disposed within the housing 14. It includes a cylindrical main chamber 26 just slightly smaller in diameter than the housing 14. The receiver 24 is shorter than the housing 14 and can, therefore, reciprocate within the housing, its travel being limited in one direction by contact with the housing front wall 16 and in the other direction by contact with its rear wall 20. A hollow tubular projection 28 of small internal diameter extends from the front of the main chamber 26 through the opening 18 in the front wall 16 of the housing 14.

A piston 30 is slidable within the main chamber 26 to vary the effective volume of the receiver 24. It is biased toward the front of the chamber 26 by a piston spring 32, which is a compression spring disposed between the back side of the piston 30 and the back wall 33 of the chamber 26.

A rod 34, encircled by the spring 32, extends from the back of the piston 30 through the opening 22 in the center of the back wall 33 of the chamber 26. There is a fluid tight seal 39 between the piston 30 and the sides of the chamber 26. Fluid in the desired quantity can be drawn into the receiver 24 through the tubular projection 28 as the piston 30 moves back into the chamber 26 against the force of the spring 32. The position of the piston 30 and the corresponding effective volume of the chamber 26 are indicated by graduation lines 40 on the rod 34.

The function of the coupling 10 is to control the flow of the fluid into and out of the receiver 24 while minimizing the quantity of included air taken in with the fluid. It is, of course, almost impossible to exclude all extraneous air down to the molecular level, but it is possible with the coupling 10 of this invention to reduce the presence of included air to levels that are acceptable for most purposes and to do so with a fairly simple and relatively inexpensive device.

In general, the coupling 10 includes a locking sleeve 42, a detent mechanism 44 for securing the coupling to a coupling receiver 46, a valve housing 48, and a valve 50 that cooperates with the coupling receiver to admit fluid to the tubular projection 28 of the fluid receiver 24.

The valve housing 48, which is generally cylindrical, is rigidly secured to the sampler housing 14, being fitted over and attached to an annular mounting 52 that extends outwardly from the front wall 16 of the sampler housing 14. The locking sleeve 42 fits over the valve housing 48 and is used to operate the detent mechanism 44 by which the coupling 19 is releasably secured to the coupling receiver 46.

Figure 2:
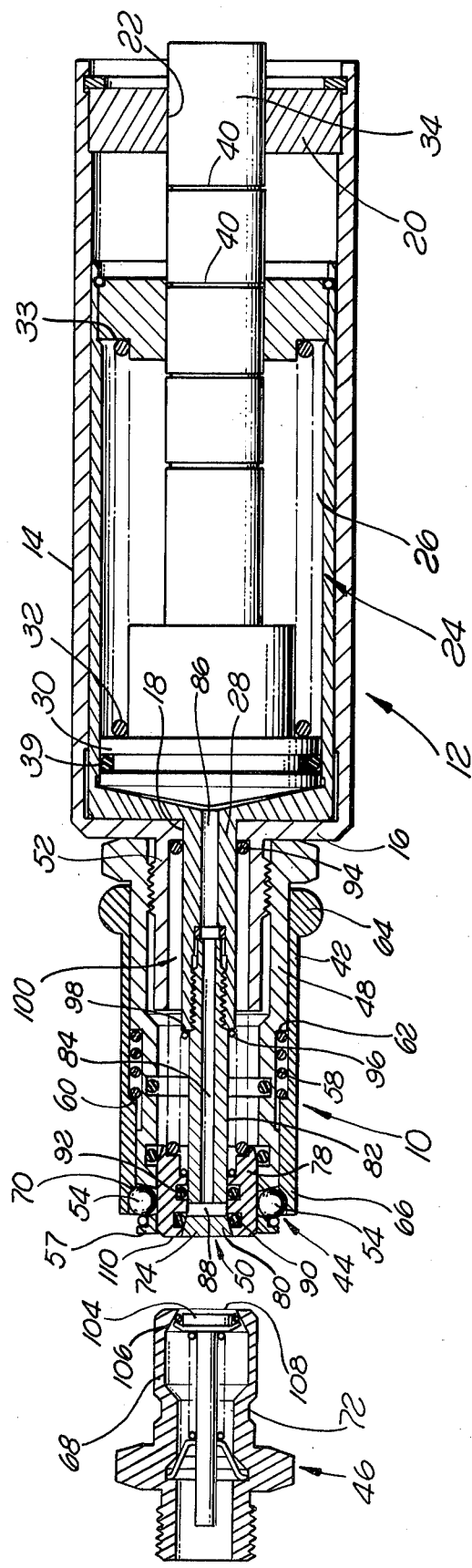
FIG. 2 is a cross-sectional side view of the sampler and a coupling receiver, shown prior to engagement.
Figure 3:
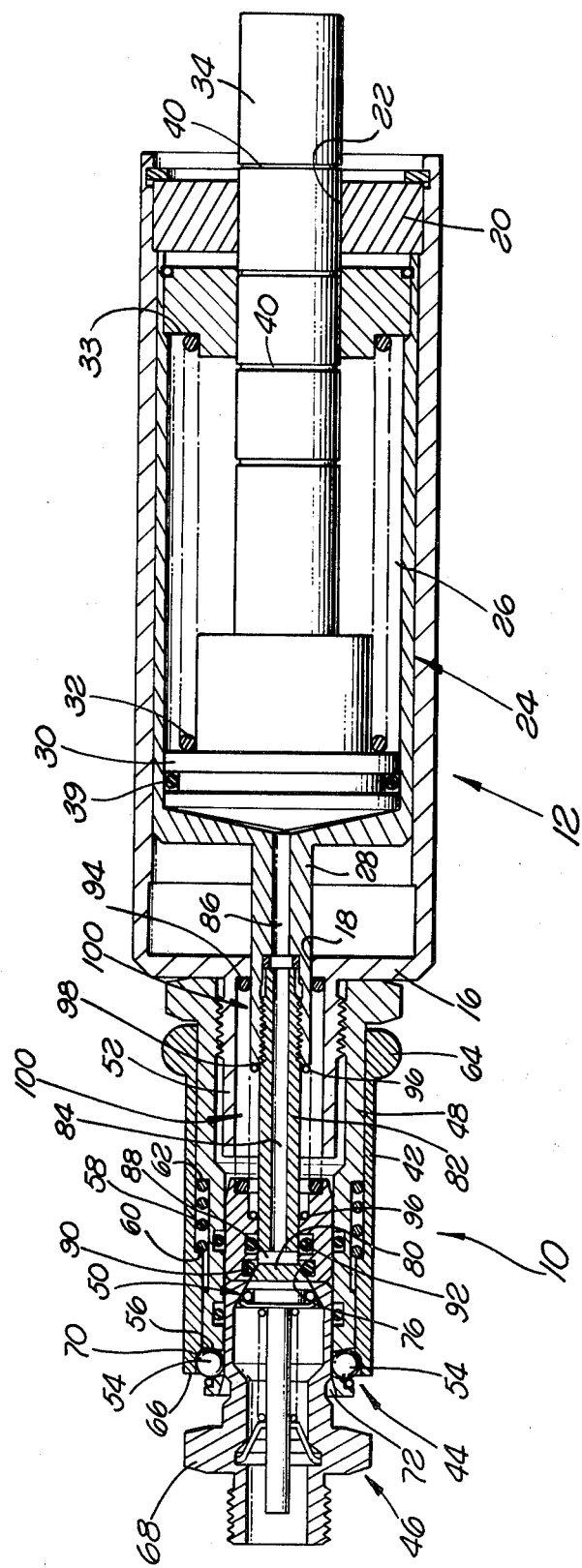
FIG. 3 is a cross-sectional view similar to FIG. 2 showing the sampler and coupling receiver in partial engagement.
Figure 4:
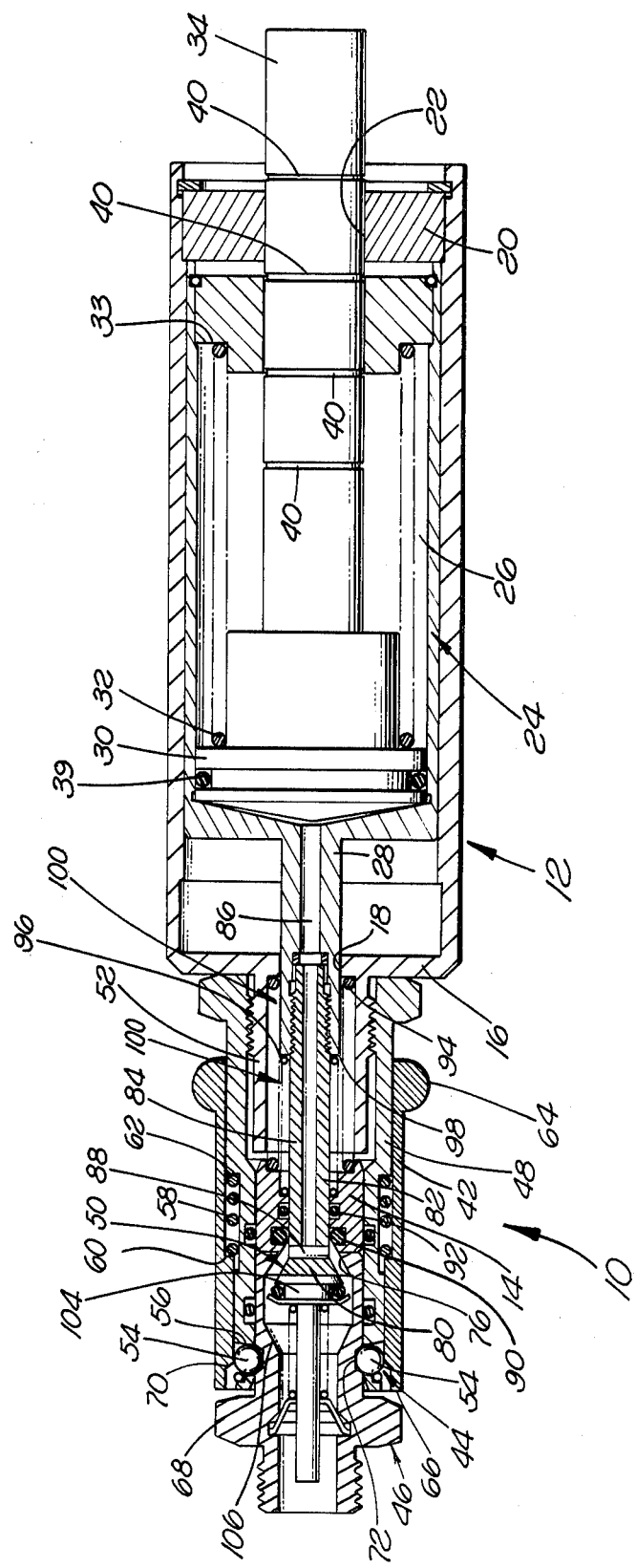
FIG. 4 is another cross-sectional view similar to FIG. 2 in which the sampler and coupling receiver are shown fully engaged.

This detent mechanism 44 is formed by a plurality of balls 54 disposed in a series of spaced-apart apertures 56 in the valve housing 48 near its front end 57. Each aperture 56 forms a ball seat approximating a part of a sphere. The seats permit the balls 54 to project beyond the inner surface of the valve housing 48, but do not permit them to pass completely through the housing 48. Normally, the inner surface of the locking sleeve 42 pushes the balls 54 radially inwardly so that they project into the interior of the housing 48 (as shown in FIGS. 1, 3 and 4). A locking compression spring 58, disposed in an annular space between the sleeve 42 and the housing valve 48 and engaging shoulders 60 and 62 on those members, urges the sleeve forward on the valve housing (away from the sampler housing 14) into this ball retaining position. The sleeve 42 can, however, be grasped by a gripping bead 64 and pulled back on the valve housing 48 so that the balls 54 are encircled by a lip 66 on the front edge of the sleeve that has a slightly larger internal diameter and allows the balls to move radially outwardly so that they do not extend beyond the inner surface of the valve housing 48. With the balls 54 thus retracted (as shown in FIG. 2), the valve housing 48 can slide snugly over a cylindrical male housing 68 of the coupling receiver 46. When the locking sleeve 42 is released, the locking spring 58 pushes it forward and a camming surface 70 on the inner edge of the lip 66 forces the balls 54 radially inwardly so that they engage an annular groove 72 on the outside of the receiver housing 68. The sampler 12 is thus secured to the coupling receiver 46 (as shown in FIGS. 3 and 4), but can be released again by simply retracting the locking sleeve 42 so that the balls 54 can move out of the groove 72.

The coupling valve 50 includes an annular valve seat 74 axially slidable within the valve housing 48. The seat 74 has a conical central opening 76, the largest diameter of which is on its outwardly facing front end. A valve closure member 78 that is slidable within the seat 74 includes a tapered head 80 shaped and dimensioned to fit tightly within the seat and a stem 82 that extends from the head into threaded engagement with the tubular projection 28 on the front end of the fluid receiver 24. The closure member 78 has an axial bore 84 that forms a continuation of a passage 86 through the hollow tubular extension 28 and ends just short of the head 80. The axial bore 84 opens to the outside of the stem 82 by a transverse cross-bore 88. The word "transverse" does not imply that the cross-bore 88 must be perpendicular to the axial bore 84, although in this preferred embodiment it is. All that is necessary is that the cross-bore 88 extend from the axial bore 84 out through the side of the closure member 78.

When the valve 50 is closed (as shown in FIGS. 2 and 3), and the closure member 78 is engaged by the seat 74, the cross-bore 88 terminates against the inner surface of the seat, and the passage 84 through the closure member is thus dead ended. The cross-bore 88 terminates between two O-ring seals 90 and 92 carried by the seat 74 so that no air can enter the axial bore 84 and the passage 86 through the cross-bore 88 when the valve 50 is closed. For the same reason, no fluid can leak out of the fluid receiver 24 when the valve 50 closed.

The valve 50 is biased toward its closed position by an outer compression spring 94 that bears against the front wall 16 of the sampler housing 14 and against the back of the seat 74. An inner compression spring 96 bears against a shoulder 98 at the front end of the tubular projection 28 and the back of the seat 74. Thus the outer spring biases the seat 74 away from the sampler housing 14, while the inner spring 96 biases it away from the fluid receiver 24. The outer spring 94 has a lower pre-load than the inner spring 96.

The above described arrangment of springs 94 and 96 forms a lost motion mechanism 100 which is highly advantageous and insures that a good airtight seal is formed between the coupling 10 and the coupling receiver 46 before the valve 50 opens. To understand this lost motion feature, it is necessary to first consider the structure of the coupling receiver 46, which is a permanent part of the fluid system (not shown) to which the sampler 12 is to be connected. Within the cylindrical coupling receiver housing 68 is a plug 104 which is axially movable and spring biased against a conical surface 106 on the inside of the housing at its leading edge. The plug 104 and the receiver housing 68 thus form a fluid tight seal in a manner similar to that of the coupling valve 50. In the case of the coupling receiver 46, however, the smallest diameter of the seat 106 is on its leading edge so that the plug 104 can move back into the housing 68, permitting fluid to flow out through the annular space between the plug and the seat. On the external side, the plug 104 and the receiver seat 106 form a single continuous planar surface 108, each member being flush with the other. On the coupling side, the seat 74 and closure member 78 are flush with each other to form one continuous planar surface 110, as shown in FIG. 2.

When the coupling 12 and coupling receiver 46 are brought together, the planar surfaces 108 and 110 engage each other without substantial air being included between them, provided that they are properly aligned. As the coupling 12 and receiver 46 are then pushed together further, the fluid path is not opened immediately. First, the valve seat 74 and closure member 78 travel together back through the valve housing 48 (lost motion) as the outer spring 94 is compressed until the partially engaged position of FIG. 3 is reached. While the outer spring 94 is being compressed, the fluid receiver 24, attached to the valve closure member 28, moves back within the sampler housing 14 until it engages back wall 20 of the housing which acts as a stop. As the coupling 12 and coupling receiver 46 thus continue to move together, the closure member 78 no longer moves relative to the sampler housing 14 and pushes the opposing plug 104 off the coupling receiver seat 106. Simultaneously, the receiver housing 68 pushes the opposing valve seat 74 off the closure member 78 by compressing the relatively stiff inner spring 96 until the fully engaged position of FIG. 4 is reached. Fluid can then flow though the annular spaces that surround the plug 104 and the closure member 78 to reach the crossbore 88, then the axial bore 84, and ultimately the fluid receiver 24. Because the lost motion mechanism 100 prevents the valve 50 and the coupling receiver 46 from opening upon initial contact, the likelihood of a misalignment between mating surfaces 108 and 110 that could admit extraneous air to the sampler 12 is greatly reduced.

To uncouple the sampler 12, the above procedure is simply reversed after the detent mechanism 44 has been released by retracting the locking sleeve 42. The coupling 10 and coupling receiver 46 cannot disengage before the valve 50 is fully closed because of the lost motion mechanism 100.

It will be noted that when the sampler 12 is disconnected, the valve seat 74 can be pressed into the valve housing 48 so that it snaps behind the balls 54 and will remain in that position unless released by retracting the locking sleeve 42. The valve 50 then acts as a relief valve. If pressure builds up in the fluid receiver 24 due to a change in temperature, the closure member 78 and fluid receiver 24 will be pushed forward by the pressure acting between the closure member and the conical surface of the seat opening 76, allowing fluid to escape and preventing damage to the sampler 12.

The coupling 10 described above admits only a minimum quantity of included air, that air being contained primarily within the bores 84 and 88 of the closure member 78. The volume of those bores 84 and 88 can be very small, using for example 1/16 inch diameter holes, since the flow rate is not of great importance and there is no mechanism that must be included within the bores.

It is important that even the small volume of the bores 84 and 88 can be eliminated as a source of included air by one sampling cycle that pre-fills this volume. The purging cycle is highly effective, almost 100 percent, because the uncomplicated and unobstructed contour of the bores 84 and 88 does not lend itself to air entrapment.

While a particular form of the invention has been illustrated and described, it will be apparent that various modifications can be made without departing from the spirit and scope of the invention.

I claim:

1. A sampler for connection to a coupling receiver of a fluid system to remove a sample of fluid from said system while minimizing the quantity of included air in said sample, said sampler comprising:
   a fluid receiver;
   a piston slidable within said fluid receiver to vary the effective volume thereof; and
   coupling means for connecting said fluid receiver to said coupling receiver, said coupling means including valve means for normally sealing said fluid receiver and for opening to admit fluid to said fluid receiver upon engagement with said coupling receiver.

2. The sampler of claim 1, wherein said coupling means further comprises a valve housing in which said valve means is slidably disposed, and lost motion means for biasing said valve means away from said fluid receiver while permitting movement of said valve means within said valve housing toward said fluid receiver before said valve means opens.

3. The sampler of claim 1, wherein said valve means comprises:
   a valve seat; and
   a valve stem engageable with said valve seat and surrounded thereby, said valve stem having a fluid passage extending axially therealong to said fluid receiver.

4. A sampler for connection to a coupling receiver of a fluid system to remove a sample of fluid from said system while minimizing the amount of included air in said sample, said sampler comprising:
   a sampler housing;
   a fluid receiver movably disposed within said sampler housing;
   means for varying the effective volume of said fluid receiver;

a valve housing mounted on said sampler housing; and valve means for admitting fluid to said fluid receiver disposed within said valve housing and operably connected to said fluid receiver for movement therewith.

5. The sampler of claim 4 further comprising lost motion means for permitting joint movement of said valve means and said fluid receiver over a predetermined distance prior to opening of said valve.

6. The sampler of claim 5 wherein said lost motion means comprises first and second springs, said first spring biasing a portion of said valve means away from said sampler housing and said second spring biasing said valve portion away from said fluid receiver.

7. The sampler of claim 5 wherein said valve means comprises a valve seat and a valve closure member surrounded by said seat, said valve seat being connected to said lost motion means and said valve closure member being connected to said fluid receiver.

8. The sampler of claim 7 further comprising a fluid passage extending through said valve closure member to said fluid receiver.

9. The sampler of claim 4 wherein said valve means comprises a valve seat and a valve closure member surrounded by said seat and slidable therein, said closure member defining a fluid passage communicating with said fluid receiver.

10. The sampler of claim 9 wherein said passageway is formed by an axial bore and a transverse bore communicating with said axial bore.

11. The sampler of claim 10 further comprising two seals carried by said valve seat, said transverse bore being disposed between said seals when said valve means is closed.

12. A sampler for connection to a coupling receiver of a fluid system to remove a sample of fluid from said system while minimizing the amount of included air in said sample, said sampler comprising:
   a sampler housing;
   a cylindrical fluid receiver slidably disposed within said sampler housing;
   a piston slidable within said fluid receiver to vary the effective volume thereof;
   a valve housing secured to said sampler housing;
   a valve seat having a conical opening and slidable within said valve housing;
   a valve closure member surrounded by said valve seat and having a tapered head shaped and dimensioned to engage said valve seat and a stem extending from said head, said valve stem having an axial bore therein and a transverse cross-bore communicating with said axial bore, said bores forming a passage by which said fluid can enter said fluid receiver when said closure member is disengaged from said valve seat, said closure member and valve seat having outer faces for engagement by said coupling receiver, said faces being flush with each other when said valve seat is engaged by said valve stem;
   a pair of spaced-apart annular seals carried by said valve seat, said cross-bore being disposed between said seals when said valve seat is engaged by said closure member;
   a first compression spring disposed between said valve seat and said sampler housing;
   a second compression spring disposed between said valve seat and said fluid receiver, thereby permitting lost motion of said valve seat and said closure member together without opening said valve upon compression of said first spring and permitting disengagement of said valve seat from said closure member stem to open said valve upon compression of said second spring, said second spring having a higher spring rate than said first spring;
   a locking sleeve surrounding said valve housing and slidable thereon; and
   detent means operable by said locking sleeve for releasably securing said coupling to a coupling receiver.

13. A coupling for connection to a coupling receiver of a fluid system which minimizes the amount of included air upon attachment of said coupling to said coupling receiver, said coupling comprising:
   a valve housing;
   a valve seat slidable within said valve housing;
   a closure member slidable within said valve seat and engageable therewith to form a fluid seal; and
   a fluid passage within said closure member and extending from said valve seat, whereby fluid can flow through said passage to said receiver.

14. The coupling of claim 13 wherein:
said passage includes an axial bore and a transverse bore; and
said valve seat carries two spaced-apart seals, said transverse bore being disposed between said seals when said closure member is engaged by said valve seat.

15. The coupling of claim 14 wherein:
said valve seat has a conical opening therein; and
said closure member has a tapered head shaped and dimensioned to be engaged by said seat and a stem extending from said head.

16. The coupling of claim 15 wherein said passage extends through said stem.

17. A coupling for connection to a coupling receiver of a fluid system which minimizes the amount of included air upon attachment of said coupling to said coupling receiver, said coupling comprising:
   a valve housing;
   a valve seat slidable within said valve housing;
   a closure member slidable within said valve seat and engageable therewith to form a fluid seal;
   an axial bore within said closure member;
   a cross-bore extending transversely within said closure member and communicating with said axial bore, said said cross-bore being exposed to admit fluid when said closure member is disengaged from said valve seat; and
   lost motion means within said housing for biasing said valve seat and said closure member toward said coupling receiver.

18. The coupling of claim 17 wherein;
said valve seat has a conical opening therein; and
said closure member has a tapered head shaped and dimensioned to be engaged by said seat and a stem extending from said head.

* * * * *